(12) United States Patent
Nagasaki et al.

(10) Patent No.: US 8,796,027 B2
(45) Date of Patent: Aug. 5, 2014

(54) NUCLEIC ACID COMPLEX AND METHOD OF INTRODUCING NUCLEIC ACID INTO CELL USING THE SAME

(75) Inventors: Takeshi Nagasaki, Hyogo (JP); Seiji Shinkai, Fukuoka (JP); Atsushi Uno, Osaka (JP); Mamoru Nishida, Chiba (JP)

(73) Assignees: JNC Corporation, Tokyo (JP); Takeshi Nagasaki, Hyogo (JP)

( * ) Notice: Subject to any disclaimer, the term of this patent is extended or adjusted under 35 U.S.C. 154(b) by 0 days.

(21) Appl. No.: 11/410,251

(22) Filed: Apr. 25, 2006

(65) Prior Publication Data

US 2006/0246585 A1 Nov. 2, 2006

(30) Foreign Application Priority Data

Apr. 27, 2005 (JP) ................. 2005-129375

(51) Int. Cl.
*C12N 15/00* (2006.01)
*C12N 15/09* (2006.01)
*A61K 38/00* (2006.01)
*A61K 47/00* (2006.01)
*C12N 15/87* (2006.01)

(52) U.S. Cl.
CPC .................... *C12N 15/87* (2013.01)
USPC ............. 435/455; 514/1.2; 530/332

(58) Field of Classification Search
CPC . A61K 2300/00; A61K 31/352; A61K 33/14; A61K 41/00; H01R 9/26
USPC .............. 435/455; 514/1.2; 530/332
See application file for complete search history.

(56) References Cited

U.S. PATENT DOCUMENTS

| 5,434,060 | A | * | 7/1995 | Hiraki et al. ................. 435/71.2 |
| 5,824,654 | A | | 10/1998 | Lavie et al. |
| 6,030,954 | A | | 2/2000 | Wu et al. |
| 6,727,347 | B1 | * | 4/2004 | Szego ............................ 530/345 |
| 2002/0130082 | A1 | * | 9/2002 | Todokoro et al. ............. 210/660 |
| 2003/0103931 | A1 | | 6/2003 | Takasaki et al. |

FOREIGN PATENT DOCUMENTS

| EP | 0 256 423 A2 | 2/1988 |
| EP | 0 256 423 A3 | 2/1988 |
| JP | 7-300563 | 11/1995 |
| JP | 11-152330 | 6/1999 |
| JP | 2000-157270 | 6/2000 |
| JP | 2003-503363 | 1/2003 |
| JP | 2003-33651 | 2/2003 |
| JP | 2003-128589 | 5/2003 |
| JP | 2003-171463 | 6/2003 |
| WO | 01/00242 | 1/2001 |

OTHER PUBLICATIONS

Schmidt-Wolf and Schmidt-Wolf. Non-viral and Hybrid Vectors in Human Gene Therapy: An Update. Trends in Molecular Medicine, 2003. 9(2):67-72.*
Yoshida et al (epsilon-Poly-L-lysine:microbial production, biodegradation and application potential. Applied Microbiol Biotechnology, 2003. 62:21-26).*
Rodríguez-Hernández et al. Biomacromolecules 2003, 4, 249-258.*
Sitohy et al. J. Agric. Food Chem. 2005, 53, 3727-3734.*
"Gene Therapy Death Prompts Review of Adenovirus Vector", Science, vol. 286, pp. 2244-2245, 1999.
S. Hacein-Bey Abina et al., "*LMO2*-Associated Clonal T Cell Proliferation in Two Patients after Gene Therapy for SCID-X1", Science, vol. 302, pp. 415-419, Oct. 17, 2003 and Erratum.
D. Chassin et al., "Dendritic cells transfected the *nef* genes of HIV-1 primary isolates specifically activate cytotoxic T lymphocytes from seropositive subjects", Eur. J. Immunol. vol. 29, pp. 196-202, 1999.
VFI Van Tendeloo et al., "Nonviral transfection of distinct types of human dendritic cells: high-efficiency gene transfer by electroporation into hematopoietic progenitor- but not monocyte-derived dendritic cells", Gene Therapy, vol. 5, pp. 700-707, 1998.
F. C. MacLaughlin et al., "Chitosan and depolymerized chitosan oligomers as condensing carriers for in vivo plasmid delivery", Journal of Controlled Release, vol. 56, pp. 259-272, 1998.
T. Ishii et al., "Mechanism of cell transfection with plasmid/chitosan complexes", Biochemica Biophysica Acta, pp. 51-64, 2001.
M. D. Brown et al., "Preliminary Characterization of Novel Amino Acid Based Polymeric Vesicles as Gene and Drug Delivery Agents", Bioconjugate Chem., vol. 11, pp. 880-891, 2000.
Granados et al., "Complexes of DNA Poly(lysine) and Poly(Nε-Trimethyllysine)", *Federation Proc.*, vol. 37, No. 6, Abstract 2051, 1978.
Pouton et al., "Polycation-DNA complexes for gene delivery: a comparison of the biopharmaceutical properties of cationic polypeptides and cationic lipids", Journal of Controlled Release, vol. 53, 1998, pp. 289-299.
Arigita et al., "Association and Dissociation Characteristics of Polymer/DNA Complexes Used for Gene Delivery", Pharmaceutical Research, vol. 16, No. 10, 1999, pp. 1534-1541.

* cited by examiner

*Primary Examiner* — Janet Epps-Smith
(74) *Attorney, Agent, or Firm* — Wenderoth, Lind & Ponack, L.L.P.

(57) ABSTRACT

A nucleic acid is effectively introduced into a cell while suppressing the cytotoxicity by administering a nucleic acid complex comprising a high molecular weight derivative of ε-poly-L-lysine and a nucleic acid to a cell.

3 Claims, 4 Drawing Sheets

SEQUENCE LISTING

```
<160> NUMBER OF SEQ ID NOS: 1

<210> SEQ ID NO 1
<211> LENGTH: 5256
<212> TYPE: DNA
<213> ORGANISM: Artificial sequence
<220> FEATURE:
<223> OTHER INFORMATION: pGL3-Control from Promega Corporation, Madison,
      WI.

<400> SEQUENCE: 1
ggtaccgagc tcttacgcgt gctagcccgg gctcgagatc tgcgatctgc atctcaatta      60
gtcagcaacc atagtcccgc ccctaactcc gcccatcccg cccctaactc cgcccagttc     120
cgcccattct ccgccccatc gctgactaat ttttttatt tatgcagagg ccgaggccgc     180
ctcggcctct gagctattcc agaagtagtg aggaggcttt tttggaggcc taggcttttg     240
caaaaagctt ggcattccgg tactgttggt aaagccacca tggaagacgc caaaaacata     300
aagaaaggcc cggcgccatt ctatccgctg aagatggaa ccgctggaga gcaactgcat     360
aaggctatga agagatacgc cctggttcct ggaacaattg cttttacaga tgcacatatc     420
gaggtggaca tcacttacgc tgagtacttc gaaatgtccg ttcggttggc agaagctatg     480
aaacgatatg ggctgaatac aaatcacaga atcgtcgtat gcagtgaaaa ctctcttcaa     540
ttctttatgc cggtgttggg cgcgttattt atcggagttg cagttgcgcc cgcgaacgac     600
atttataatg aacgtgaatt gctcaacagt atgggcattt cgcagcctac cgtggtgttc     660
gtttccaaaa aggggttgca aaaattttg aacgtgcaaa aaaagctccc aatcatccaa     720
aaaattatta tcatggattc taaaacggat taccagggat ttcagtcgat gtacacgttc     780
gtcacatctc atctacctcc cggttttaat gaatacgatt ttgtgccaga gtccttcgat     840
agggacaaga caattgcact gatcatgaac tcctctggat ctactggtct gcctaaaggt     900
gtcgctctgc tcatagaac tgcctgcgtg agattctcgc atgccagaga tcctattttt     960
ggcaatcaaa tcattccgga tactgcgatt ttaagtgttg ttccattcca tcacggtttt    1020
ggaatgttta ctacactcgg atatttgata tgtggatttc gagtcgtctt aatgtataga    1080
tttgaagaag agctgtttct gaggagcctt caggattaca agattcaaag tgcgctgctg    1140
gtgccaaccc tattctcctt cttcgccaaa agcactctga ttgacaaata cgatttatct    1200
aatttacacg aaattgcttc tggtggcgct cccctctcta aggaagtcgg ggaagcggtt    1260
gccaagaggt tccatctgcc aggtatcagg caaggatatg ggctcactga gactacatca    1320
gctattctga ttacacccga gggggatgat aaaccgggcg cggtcggtaa agttgttcca    1380 tttttgaag cgaaggttgt ggatctggat accgggaaaa cgctgggcgt taatcaaga    1440 ggcgaactgt gtgtgagagg tcctatgatt atgtccggtt atgtaaacaa tccggaagcg    1500
accaacgcct tgattgacaa ggatggatgg ctacattctg gagacatagc ttactgggac    1560
gaagacgaac acttcttcat cgttgaccgc ctgaagtctc tgattaagta caaaggctat    1620
caggtggctc ccgctgaatt ggaatccatc ttgctccaac accccaacat cttcgacgca    1680
ggtgtcgcag gtcttcccga cgatgacgcc ggtgaacttc ccgccgccgt tgttgttttg    1740
gagcacggaa agacgatgac ggaaaaagag atcgtggatt acgtcgccag tcaagtaaca    1800
```

```
accgcgaaaa agttgcgcgg aggagttgtg tttgtggacg aagtaccgaa aggtcttacc   1860
ggaaaactcg acgcaagaaa aatcagagag atcctcataa aggccaagaa gggcggaaag   1920
atcgccgtgt aattctagag tcggggcggc cggccgcttc gagcagacat gataagatac   1980
attgatgagt ttggacaaac cacaactaga atgcagtgaa aaaatgctt tatttgtgaa    2040
atttgtgatg ctattgcttt atttgtaacc attataagct gcaataaaca agttaacaac   2100
aacaattgca ttcattttat gtttcaggtt caggggagg tgtgggaggt ttttaaagc    2160
aagtaaaacc tctacaaatg tggtaaaatc gataaggatc tgaacgatgg agcggagaat   2220
gggcggaact gggcggagtt aggggcggga tgggcggagt taggggcggg actatggttg   2280
ctgactaatt gagatgcatg ctttgcatac ttctgcctgc tggggagcct ggggactttc   2340
cacacctggt tgctgactaa ttgagatgca tgctttgcat acttctgcct gctggggagc   2400
ctggggactt ccacaccct aactgacaca cattccacag cggatccgtc gaccgatgcc   2460
cttgagagcc ttcaacccag tcagctcctt ccggtgggcg cggggcatga ctatcgtcgc   2520
cgcacttatg actgtcttct ttatcatgca actcgtagga caggtgccgg cagcgctctt   2580
ccgcttcctc gctcactgac tcgctgcgct cggtcgttcg gctgcggcga gcggtatcag   2640
ctcactcaaa ggcggtaata cggttatcca gaatcagg gataacgca ggaaagaaca   2700
tgtgagcaaa aggccagcaa aaggccagga accgtaaaaa ggccgcgttg ctggcgtttt   2760
tccataggct ccgcccccct gacgagcatc acaaaaatcg acgctcaagt cagaggtggc   2820
gaaacccgac aggactataa agataccagg cgtttccccc tggaagctcc ctcgtgcgct   2880
ctcctgttcc gaccctgccg cttaccggat acctgtccgc ctttctccct tcgggaagcg   2940
tggcgctttc tcatagctca cgctgtaggt atctcagttc ggtgtaggtc gttcgctcca   3000
agctgggctg tgtgcacgaa ccccccgttc agcccgaccg ctgcgcctta ccggtaact   3060
atcgtcttga gtccaacccg gtaagacacg acttatcgcc actggcagca gccactggta   3120
acaggattag cagagcgagg tatgtaggcg gtgctacaga gttcttgaag tggtggccta   3180
actacggcta cactagaaga acagtatttg gtatctgcgc tctgctgaag ccagttacct   3240
tcggaaaaag agttggtagc tcttgatccg gcaaacaaac caccgctggt agcggtggtt   3300
tttttgtttg caagcagcag attacgcgca gaaaaaagg atctcaagaa gatcctttga   3360
tcttttctac ggggtctgac gctcagtgga acgaaaactc acgttaaggg attttggtca   3420
tgagattatc aaaaaggatc ttcacctaga tccttttaaa ttaaaaatga agttttaaat   3480
caatctaaag tatatatgag taaacttggt ctgacagtta ccaatgctta atcagtgagg   3540
cacctatctc agcgatctgt ctatttcgtt catccatagt tgcctgactc cccgtcgtgt   3600
agataactac gatacgggag ggcttaccat ctggccccag tgctgcaatg ataccgcgag   3660
acccacgctc accggctcca gatttatcag caataaacca gccagccgga agggccgagc   3720
gcagaagtgg tcctgcaact ttatccgcct ccatccagtc tattaattgt tgccgggaag   3780
ctagagtaag tagttcgcca gttaatagtt tgcgcaacgt tgttgccatt gctacaggca   3840
tcgtggtgtc acgctcgtcg tttggtatgg cttcattcag ctccggttcc caacgatcaa   3900
ggcgagttac atgatccccc atgttgtgca aaaaagcggt tagctccttc ggtcctccga   3960
tcgttgtcag aagtaagttg gccgcagtgt tatcactcat ggttatggca gcactgcata   4020
attctcttac tgtcatgcca tccgtaagat gcttttctgt gactggtgag tactcaacca   4080
agtcattctg agaatagtgt atgcggcgac cgagttgctc ttgcccggcg tcaatacggg   4140
```

```
ataataccgc gccacatagc agaactttaa aagtgctcat cattggaaaa cgttcttcgg    4200
ggcgaaaact ctcaaggatc ttaccgctgt tgagatccag ttcgatgtaa cccactcgtg    4260
cacccaactg atcttcagca tcttttactt tcaccagcgt ttctgggtga gcaaaaacag    4320
gaaggcaaaa tgccgcaaaa aagggaataa gggcgacacg gaaatgttga atactcatac    4380
tcttcctttt tcaatattat tgaagcattt atcagggtta ttgtctcatg agcggataca    4440
tatttgaatg tatttagaaa aataaacaaa taggggttcc gcgcacattt ccccgaaaag    4500
tgccacctga cgcgcccctgt agcggcgcat taagcgcggc gggtgtggtg gttacgcgca    4560
gcgtgaccgc tacacttgcc agcgccctag cgcccgctcc tttcgctttc ttcccttcct    4620
ttctcgccac gttcgccggc tttccccgtc aagctctaaa tcggggggctc cctttaggggt   4680
tccgatttag tgctttacgg cacctcgacc ccaaaaaact tgattagggt gatggttcac    4740
gtagtgggcc atcgccctga tagacggttt ttcgcccttt gacgttggag tccacgttct    4800
ttaatagtgg actcttgttc caaactggaa caacactcaa ccctatctcg gtctattctt    4860
ttgatttata agggattttg ccgatttcgg cctattggtt aaaaaatgag ctgatttaac    4920
aaaaatttaa cgcgaatttt aacaaaatat taacgcttac aatttgccat tcgccattca    4980
ggctgcgcaa ctgttgggaa gggcgatcgg tgcgggcctc ttcgctatta cgccagccca    5040
agctaccatg ataagtaagt aatattaagg tacgggaggt acttggagcg gccgcaataa    5100
aatatcttta ttttcattac atctgtgtgt tggttttttg tgtgaatcga tagtactaac    5160
atacgctctc catcaaaaca aaacgaaaca aaacaaacta gcaaatagg ctgtccccag     5220
tgcaagtgca ggtgccagaa catttctcta tcgata                              5256
```

NUCLEIC ACID COMPLEX AND METHOD OF INTRODUCING NUCLEIC ACID INTO CELL USING THE SAME

BACKGROUND OF THE INVENTION

1. Field of the Invention

The present invention relates to a nucleic acid complex comprising a high molecular weight derivative of ε-poly-L-lysine and a nucleic acid, and a method of introducing a nucleic acid complex into a cell, comprising administering the nucleic acid complex to a cell.

2. Description of the Related Art

Conventionally, methods of introducing a nucleic acid such as a gene into a cell are broadly classified into: introduction methods using chemical or physical means (nonviral method) such as the calcium phosphate method, polymer method such as DEAE-dextran method, liposome method, electroporation method, and microinjection method; and biological methods (viral method) utilizing a viral vector such as adenovirus vector or retrovirus vector, all of which are widely utilized.

Meanwhile, the biological method utilizing the infectivity of a virus has the advantage of a high gene introduction and expression efficiency, but it is pointed out that it has problems relating to safety of the virus itself, such as immunogenicity, probability of recurrence of pathogenicity and cell canceration, and the accidents actually happened (Marshall, E., et al., Science, 286, 2244 (1999), and Hacein-Bey-Abina, S. et al., Science, 302, 415 (2003)).

On the other hand, great expectations for the nonviral methods have been raised, because of its advantages including lower risks for safety compared with the viral method, easiness in a procedure of introducing a nucleic acid, and availability of an inexpensive, large-scale preparation of an introduction agent. However, it is a significant issue to be improved that the method has lower introduction and expression efficiency than a viral vector. To increase the efficiency of the nonviral methods, it is required to overcome several problems such as cell selectivity, cell membrane-permeability, nuclease-resistance, nuclear entry efficiency, nucleic acid releasability, and the like. As in the viral method, the nonviral methods also have important issues of safety assurance such as decrease in toxicity to a living body or a cell.

The liposome method, which is one of the chemical methods, has advantages in that a lipid in a liposome membrane is easy to interact with a cell membrane or an intracellular organ and has low antigenecity because it is composed of the same lipids as a biomembrane in most cases. However, gene introduction by means of a liposome has a disadvantage in that it is hardly provided for a practical use owing to problems such as low gene expression efficiency and high cytotoxicity (Chassin, D. et al., Eur. J. Immunol., 29, 196 (1999), and Van Tendeloo, V. F. et al., Gene Ther., 5, 700 (1998)).

Examples of typical chemical means include the polymer method as well as the liposome method. The polymer method draws attention as a nonviral method that enables various functionalizations by chemical modification. Among polymeric substances, polyethyleneimine that is a cationic polymer has an excellent ability for DNA compaction, which gives high introduction efficiency. However, it has a disadvantage of extremely strong cytotoxicity. Therefore, to solve the problem relating to safety such as cytotoxicity, it is necessary to impart biodegradability or biocompatibility to polymers, and there has also been studied a technique using a naturally derived cationic polymer that inherently has biodegradability or biocompatibility. Among polysaccharides, α-glucan-based dextran and β-1,4-glucosamine-based chitosan derivatives have been studied. However, DEAE-dextran or the like has a problem of extremely strong cytotoxicity, and chitosan also has problems that conditions for forming a DNA complex are limited and that a large amount of DNA is required for a sufficient gene expression (MacLaughlin, F. C. et al., J. Controlled Rel., 56, 259 (1998), and Ishii, T. et al., Biochim. Biophys. Acta, 1514, 51(2001), and JP 2000-157270 A).

Also, cationic polypeptides have been examined as gene introduction agents, and in particular, many studies have been made on α-poly-L-lysine because it has ability for DNA compaction. However, α-poly-L-lysine is known to have problems such as an insufficient gene introduction activity, high aggregation of a DNA complex, and high cytotoxicity (Brown, M. D. et al., Bioconjug. Chem., 11, 880 (2000)).

Therefore, in order to introduce a nucleic acid into a cell, development of a nucleic acid introduction agent which can be prepared easily and inexpensively, and has low cytotoxicity, and has excellent nucleic acid introduction efficiency, and an introduction method using the same has been strongly desired.

SUMMARY OF THE INVENTION

An object of the present invention is to provide: a nucleic acid complex that has a high introduction efficiency of a nucleic acid into a cell with low cytotoxicity, and can be prepared easily and inexpensively; and a method of introducing a nucleic acid into a cell using the nucleic acid complex with safety and high transfection efficiency.

The inventors of the present invention have made extensive studies to solve the above-described object. As a result, they have found that a high molecular weight derivative of ε-poly-L-lysine, which is a naturally derived cationic polymer having excellent biocompatibility and biodegradability, forms a strong complex with a nucleic acid electrostatically, and that the nucleic acid complex comprising the high molecular weight derivative and a nucleic acid has a gene introduction efficiency dramatically higher than that of a conventional polymer and nucleic acid complex and has low cytotoxicity, and the present invention has been accomplished based on these findings.

It is an object of the present invention to provide a nucleic acid complex, comprising a high molecular weight derivative of ε-poly-L-lysine which is obtained by using the ε-poly-L-lysine represented by the following Formula (I) and a nucleic acid.

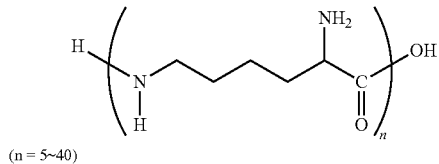

(n = 5~40)

It is a further object of the present invention to provide the nucleic acid complex as described above, wherein the high molecular weight derivative has a molecular weight of 5,000 to 100,000.

It is a further object of the present invention to provide the nucleic acid complex as described above, wherein the high molecular weight derivative is obtained by dehydration-condensation of the ε-poly-L-lysine represented by Formula (I).

It is a further object of the present invention to provide the nucleic acid complex as described above, wherein the high molecular weight derivative is obtained by irradiating the ε-poly-L-lysine represented by Formula (I) with radiation.

It is a further object of the present invention to provide the nucleic acid complex as described above, wherein the high molecular weight derivative is obtained by a reaction of the ε-poly-L-lysine represented by Formula (I) with a crosslinker.

It is a further object of the present invention to provide the nucleic acid complex as described above, wherein the ε-poly-L-lysine represented by Formula (I) is produced by microbial fermentation.

It is a further object of the present invention to provide the nucleic acid complex as described above, wherein the nucleic acid is a plasmid DNA.

It is a further object of the present invention to provide a method of introducing a nucleic acid into a cell, comprising administering the nucleic acid complex as described above to a cell.

DETAILED DESCRIPTION OF EXEMPLARY EMBODIEMENTS

Figure 1:
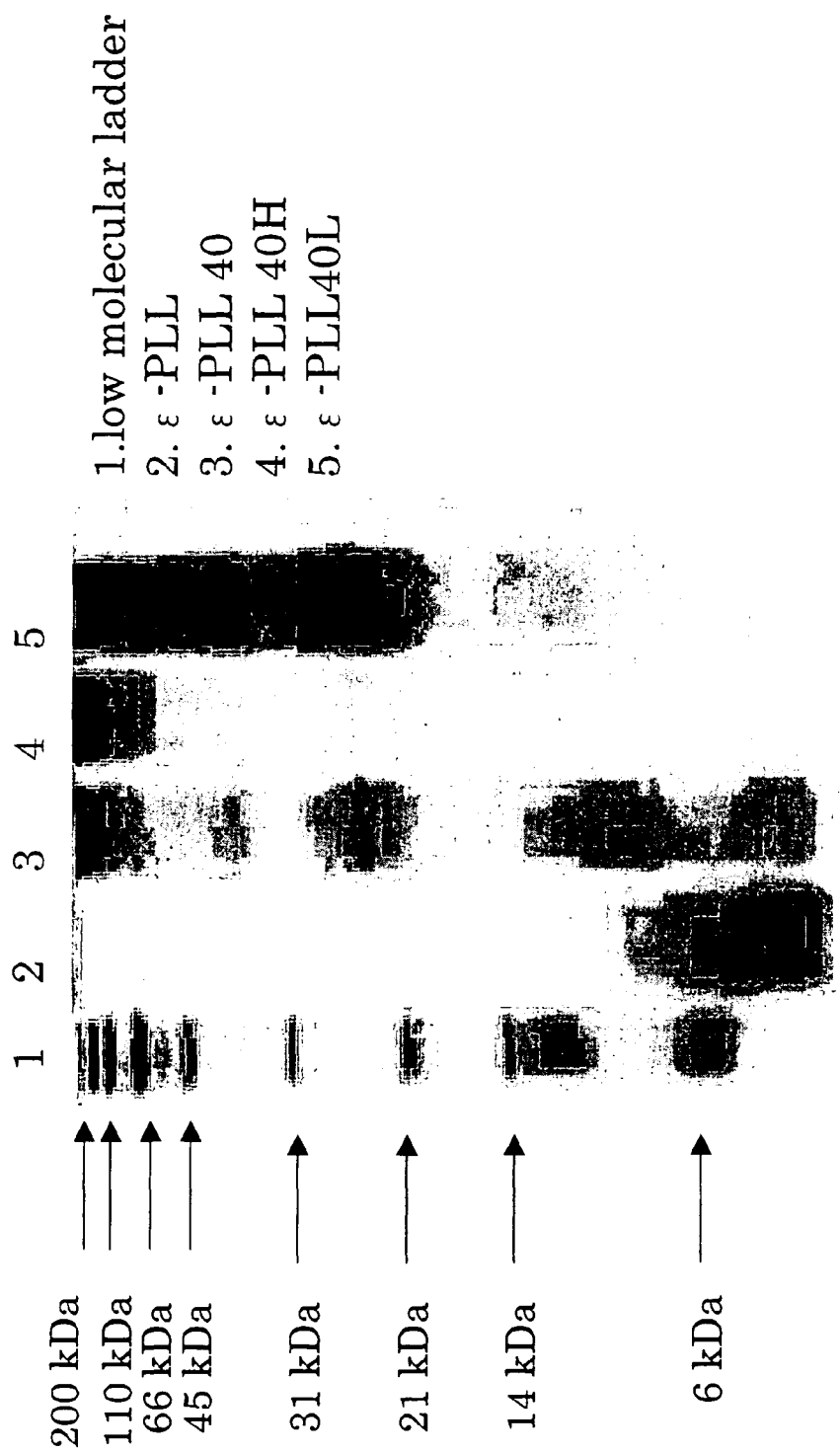
FIG. 1 shows the results of SDS-PAGE for the high molecular weight ε-poly-L-lysine (Example 1).

ε-poly-L-lysine, which is represented by the Formula (I) as shown above and can be used for obtaining the high molecular weight derivative of ε-poly-L-lysine of the present invention, can be obtained by any methods including biological methods using a microorganism and chemical synthesis from lysine. Since it is difficult to synthesize ε-poly-L-lysine by a chemical procedure and chemical synthesis requires high costs, ε-poly-L-lysine produced by a microorganism is preferably used. For example, ε-poly-L-lysine can be obtained by: culturing Streptomyces alubulus ssp. lysinopolymerus described in JP 1245361 B in a medium; and separating and collecting ε-poly-L-lysine from the resultant culture. An example of the medium for culturing Streptomyces alubulus ssp. lysinopolymerus includes a medium containing 5 wt % glucose, 0.5 wt % yeast extract, 1 wt % ammonium sulfate, 0.08 wt % dipotassium hydrogen phosphate, 0.136 wt % potassium dihydrogen phosphate, 0.05 wt % magnesium sulfate heptahydrate, 0.004 wt % zinc sulfate heptahydrate, and 0.03 wt % iron sulfate heptahydrate, which is adjusted to pH 6.8. Furthermore, commercially available ε-poly-L-lysine may also be used.

The high molecular weight derivative of ε-poly-L-lysine of the present invention (hereafter, referred to as "high molecular weight ε-poly-L-lysine") may be one obtained by any method, and examples thereof include one obtained by exposure to radiation as described in JP 3502879 B and one prepared by using a crosslinker as described in JP 2003-171464 A. Crosslinkers used in the present invention include ethylene glycol diglycidyl ether, polyethylene glycol diglycidyl ether, propylene glycol diglycidyl ether, polypropylene glycol diglycidyl ether, neopenthyl glycol diglycidyl ether, 1,6-hexanediol diglycidyl ether, glycerol diglycidyl ether, glycerol triglycidyl ether, trimethylolpropane glycidyl ether, and trimethylolpropane triglycidyl ether. Furthermore, one obtained by linking with a crosslinker using an enzyme such as transglutaminase may also be used. However, the exposure to radiation requires expensive mechanical appliances, and the preparation requires advanced production control. The linking with a crosslinker requires some long period of the reaction step and cumbersome procedures such as removal of unreacted components. An example of a high molecular weight ε-poly-L-lysine to be obtained easily in a short time includes a high molecular weight ε-poly-L-lysine that is described in JP 2003-1714632 A and is obtained by a dehydration-condensation reaction by heat-treatment of ε-poly-L-lysine obtained from microbial fermentation under an inert gas atmosphere or under vacuum at a temperature of 150° C. or more.

The molecular weight of the high molecular weight ε-poly-L-lysine to be used in the present invention is preferably 5,000 to 100,000, more preferably 10,000 to 70,000, further more preferably 10,000 to 50,000 in terms of introduction efficiency of a nucleic acid and cytotoxicity.

A method of fractionating the high molecular weight ε-poly-L-lysine to be used in the present invention according to respective molecular weights may be any method, and examples thereof include the gel filtration chromatography method, ultrafiltration method, ion exchange chromatography method, and preparative SDS-PAGE method.

A nucleic acid to be used in the present invention may be a relatively short nucleic acid regardless of a single- or double-strand (DNA, RNA), that is, nucleic acid fragments having a length of 1 kilobase (kb) or less in general, about 500 bases or less inmost cases. Also, there can be applied one having a length of 1 kb or more in general, about 3 kb to 10 kb in most cases, such as a plasmid DNA that is a double-stranded nucleic acid including a gene encoding an intended protein as well as a promoter and terminator necessary for expression of such a protein.

As described above, in the present invention, a plasmid DNA, which contains a gene encoding a protein to be expressed downstream of a promoter, can be also used as a nucleic acid substance to be introduced into a cell. Its specific sequence varies depending on an intended protein.

Also, a cell into which a plasmid DNA is introduced is not limited and includes all kinds of culture and primary animal cells selected depending on the purpose such as therapy of a disease or cloning. Meanwhile, the nucleic acid complex of the present invention is also effective in administration to a living body. As a method of administering the plasmid DNA to a living body, parenteral administration (intravenous administration), aerosol inhalation, subcutaneous injection, intraperitoneal injection, or intramuscular injection can be performed.

Conditions for formation of the nucleic acid complex are not particularly limited, but, for example, the complex may be prepared simply by: mixing the high molecular weight ε-poly-L-lysine and a nucleic acid in an appropriate solvent; and then, leaving it to stand for about 30 minutes. The mixing ratio of the high molecular weight ε-poly-L-lysine to a plasmid DNA is 1 to 25, preferably 5 to 15 of N/P ratio. Herein, the N/P ratio is a value calculated by dividing the number of nitrogen atoms capable of being protonated in the high molecular weight ε-poly-L-lysine by the number of anions in the DNA. Protonation of the half of the nitrogen atoms in ε-poly-L-lysine may change all the nitrogen atoms to cations, so that the number of cations may be estimated to be the half of the number of all the nitrogen atoms. With regard to the number of anions, one nucleotide residue that constitutes DNA is regarded as one anion. The average molecular weight of a nucleotide can be assumed to be 325, and the number of anions can be calculated from the amount of DNA used.

The amount for addition of the complex comprising the high molecular weight ϵ-poly-L-lysine and a nucleic acid of the present invention with respect to a certain number of cells is not particularly limited and may be appropriately selected by a person skilled in the art depending on the kinds of cells, the kinds of nucleic acids, the amount of a nucleic acid to be introduced into a cell, or the like. Also, the standing time is not limited and may be appropriately selected by a person skilled in the art depending on the kinds of compounds or nucleic acids of the present invention, or the like. For example, 0.5 to 5 hours, preferably 2 to 5 hours are exemplified as the standing time. Meanwhile, the complex of the high molecular weight ϵ-poly-L-lysine/anionic plasmid DNA is formed mainly by electrostatic aggregation, and it can form a complex in an aqueous medium.

More specific methods for preparing the transfection agent, characterization thereof, and methods and evaluation of administration in vitro are exemplified in detail in the following examples.

EXAMPLES

Hereinafter, the present invention will be described more specifically by referring to the examples, but the present invention is not limited to the following examples.

Example 1

Preparation of High Molecular Weight ϵ-poly-L-lysine 100 mg of ϵ-poly-L-lysine (ϵ-PLL, number-average molecular weight 4,000, manufactured by Chisso Corporation) was placed in a glass microtube and was subjected to dehydration-condensation in vacuum at 185° C. for 40 minutes using a glass tube oven (Shibata GTO-350-RD, manufactured by Sibata Scientific Technology Ltd.). Hereafter, the resultant derivative obtained by the dehydration-condensation for 40 minutes is referred to as ϵ-PLL40.

Molecular Weight Fractionation of High Molecular Weight ϵ-poly-L-lysine

ϵ-PLL40 (50 mg) was dissolved in 10 ml of ultrapure water (milliQ, manufactured by Millipore Corporation), and components having a molecular weight of 50,000 or more were fractionated using an ultrafiltration filter [Centriplus YM-50 (manufactured by Millipore Corporation)]. Hereafter, a fraction having a molecular weight of 50,000 or more is referred to as ϵ-PLL40H. The obtained filtrate was used to further fractionate components having a molecular weight of 10,000 or more using an ultrafiltration filter [Centricon Plus-20 (manufactured by Millipore Corporation)]. Hereafter, a fraction having a molecular weight of 10,000 to 50,000 is referred to as ϵ-PLL40L. The obtained fractions each having a molecular weight of 50,000 or more (ϵ-PLL40H) or 10,000 to 50,000 (ϵ-PLL40L) were separately placed in sample tubes and frozen by means of liquid nitrogen, followed by freeze-drying, to yield 12 mg of ϵ-PLL40L and 10 mg of ϵ-PLL40H as white powder, respectively. Table 1 shows elemental analysis values (wt %) and the numbers of nitrogen capable of being protonated calculated from the wt % of N.

TABLE 1

Elemental analysis values and numbers of protonated nitrogen of the high molecular weight ϵ-poly-L-lysine

| Sample names | Elemental analysis values (%) | | | Numbers of protonated nitrogen µmol/mg |
|---|---|---|---|---|
| | C | H | N | |
| ϵ-PLL | 53.86 | 8.85 | 20.35 | 7.26 |
| ϵ-PLL40 | 55.65 | 9.50 | 21.41 | 7.64 |
| ϵ-PLL40L | 52.15 | 9.02 | 18.95 | 6.76 |
| ϵ-PLL40H | 51.41 | 9.07 | 17.73 | 6.33 |

Evaluation of Molecular Weight by SDS-PAGE

Electrophoresis was performed using a separation gel having an acrylamide concentration of 15 w/v %. 3 µl of an electrophoresis sample (1 mg/ml) was added with 2 µl of ultrapure water (milliQ) and 5 µl of 2× sample buffer (0.125 M (mol/l) Tris buffer containing 10 w/v % 2-mercaptoethanol, 4 w/v % SDS, and 10 w/v % sucrose) to prepare a sample solution, and the solution was boiled at 95° C. for 3 minutes. Electrophoresis was performed at 100 V and 30 mA for about 2 hours, and then the gel was stained with Coomassie Brilliant Blue solution overnight. After that, the gel was decolored for about 12 hours, and an electrophoresis image was taken. The results are shown in FIG. 1.

Most of the components having a molecular weight of 10,000 or less disappeared by the heat treatment. Meanwhile, ϵ-PLL40H was found to contain few components having a molecular weight of 50,000 or less as a result of the molecular weight fractionation. On the other hand, ϵ-PLL40L was found to contain components having a molecular weight of 50,000 or less as primary components.

Example 2

Preparation of Plasmid DNA Complex

The high molecular weight ϵ-poly-L-lysine, which was obtained in Example 1 and subjected to the molecular weight fractionation, was used to prepare 10 w/v % PBS solution having a concentration of nitrogen atoms capable of being protonated of 7.7 mM (mmol/L) (if necessary, a heat/ultrasonic treatment was performed upon dissolution). For each condition, 5 µl of 0.2 µg/µl pGL3-Control (a plasmid DNA encoding luciferase for COS-1: SEQ ID NO: 1) solution and a predetermined volume of the high molecular weight ϵ-poly-L-lysine solution were added into 10 w/v % PBS solution (50 µl) and mixed to form a DNA complex.

Comparative Example 1

A plasmid DNA complex was prepared in a manner similar to Example 2 except that the high molecular weight ϵ-poly-L-lysine in Example 2 was replaced by ϵ-poly-L-lysine (ϵ-PLL, number-average molecular weight 4,000, manufactured by Chisso Corporation), polyethyleneimine (PEI, molecular weight 25,000, manufactured by Aldrich Corporation), and α-polylysine (α-PLL, molecular weight 5,000 to 15,000, manufactured by Wako Pure Chemical Industries, Ltd.), respectively.

Confirmation of Formation of the DNA Complex by Gel Electrophoresis Method

A plasmid DNA is electrophoresed toward the positively-charge direction due to its negatively charged phosphate groups. Since it migrates through openings of network of a gel matrix, the mobility becomes the lower as the molecular weight of the plasmid DNA becomes the larger by forming a complex with a polycationic modified polymer. Accordingly, in the manner described in Example 2 and Comparative Example 1, various amounts of high molecular weight ε-poly-L-lysine, ε-poly-L-lysine, polyethyleneimine, and α-polylysine were added to a certain amount of the plasmid DNA to form complexes having various rate of the amount of cations in amino groups/the amount of anions in phosphoric acid (N/P). After that, the complexes were electrophoresed on a 1 w/v % agarose gel at 100 V for 40 minutes, followed by staining with ethidium bromide, and their mobilities were evaluated by means of a transilluminator.

Figure 2:
FIG. 2 shows the results obtained by confirming molecular weights of the formed DNA complexes by a gel electrophoresis method.

The results are shown in FIG. 2. The results of the agarose gel electrophoresis revealed that the mobilities of the plasmid DNAs were decreased as the amounts of the added samples increased, thus the formation of the complexes was confirmed. The high molecular weight ε-poly-L-lysine in Example 2 was clearly found to have increased affinity to the plasmid DNA compared with ε-poly-L-lysine (ε-PLL) and α-polylysine in Comparative Example 1, although the affinity is weaker than that of polyethyleneimine (PEI).

Example 3

Transfection Procedure and Quantification of Expressed Protein

The high molecular weight ε-poly-L-lysine obtained in Example 1 was used to introduce pGL3-Control, which is a plasmid DNA encoding luciferase, into COS-1 (African green monkey kidney cell) for evaluation of the expression.

There was prepared solution of the high molecular weight ε-poly-L-lysine dissolved in 10 w/v % PBS having a concentration of nitrogen atoms capable of being protonated of 7.7 mM (if necessary, a heat/ultrasonic treatment was performed upon dissolution). For each well, 5 μl of 0.2 μg/μl pGL3-Control solution and a predetermined amount of solution of the high molecular weight ε-poly-L-lysine in 10 w/v % PBS were added into 10 w/v % PBS (50 μl) and mixed to form a DNA complex.

3 to $4 \times 10^4$ cells/well of COS-1 was inoculated to a 24-well microtiter plate and cultured in a DME medium containing 10 w/v % fetal bovine serum at 37° C. in 5 v/v % $CO_2$ overnight, and then, the medium was removed using an aspirator. After that, 200 μl/well of a fresh medium having a concentration 1.25 times higher than the normal concentration was added. The above-described DNA complex solution (50 μl) was added thereto, and the cells were cultured at 37° C. for 3 hours to introduce the complex into the cells. Then, the medium was removed using an aspirator, and 1 ml/well of a fresh medium was added, followed by culturing at 37° C. for 48 hours.

The expression levels of luciferase in cultured cells were determined with reference to the following document using Steady-Glo Luciferase Assay System (manufactured by Progema Corporation) in accordance with the protocol to quantify chemiluminescence levels, which were defined as transfection activities. At that time, a lumino-plate reader (manufactured by ThermoLab Systems, FluoroAcent EL) was used.

Reference Document: Wood, K. V. (1991) In: Bioluminescence and Chemiluminescence: Current Status, Stanley, P. and Kricka, L., eds., John Wiley and Sons, Chichester, N.Y., 11.

Comparative Example 2

Transfection and quantification of the expressed protein were performed in a manner similar to Example 3 except that the high molecular weight ε-poly-L-lysine used in Example 3 was replaced by ε-poly-L-lysine (ε-PLL, number-average molecular weight 4,000, manufactured by Chisso Corporation), polyethyleneimine (PEI, molecular weight 25,000, manufactured by Aldrich Corporation), and α-polylysine (α-PLL, molecular weight 5,000 to 15,000, manufactured by Wako Pure Chemical Industries, Ltd.), respectively.

Figure 3:
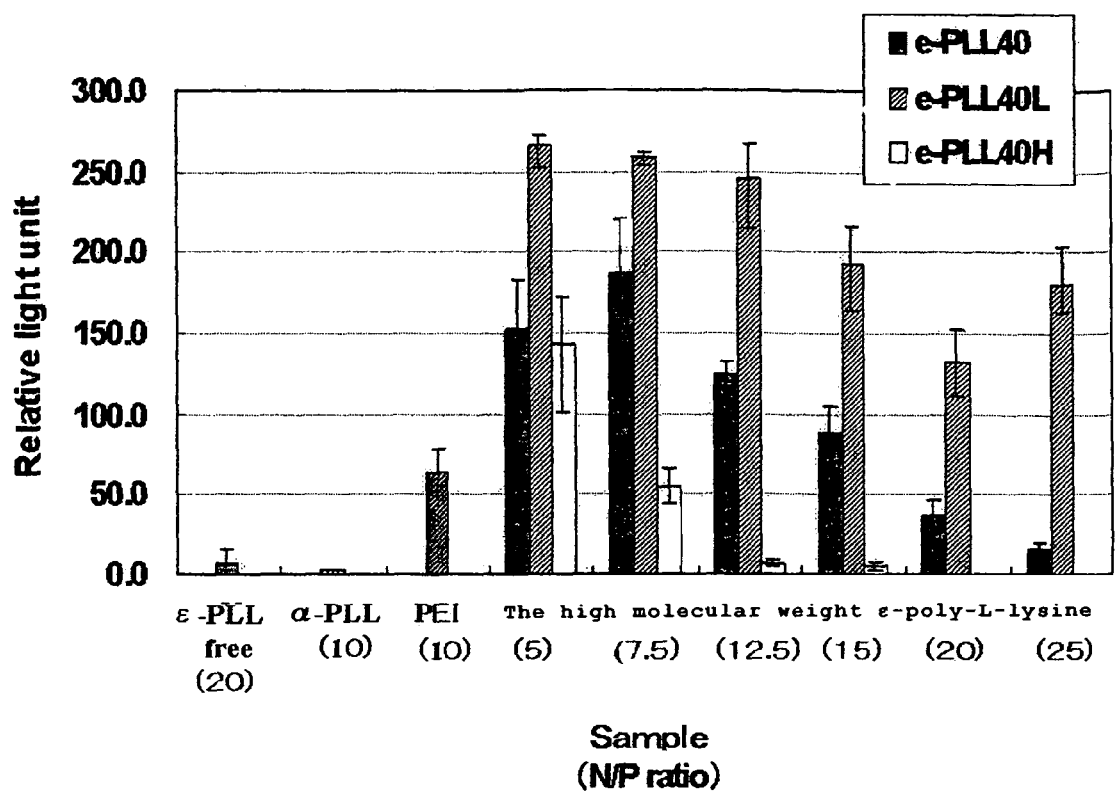
FIG. 3 shows the transfection activities of the high molecular weight ε-poly-L-lysine.

The results are shown in FIG. 3. In the case of the high molecular weight ε-poly-L-lysine, the activity of the expressed protein was higher than that in the case of polyethyleneimine (PEI), which is a polyamine-based transfection agent and used in Comparative Example 2. Meanwhile, with regard to the expression efficiency, the activity was 20 or more times higher than that in the case of E-poly-L-lysine (ε-PLL). In particular, ε-PLL40L, which was obtained by fractionation of components having a molecular weight of 10,000 to 50,000, was found to exhibit an excellent transfection activity and considered to be effective as a transfection agent. The results clearly show that the high molecular weight ε-poly-L-lysine has a much more excellent transfection activity than α-polylysine.

Evaluation of Cytotoxicity

The high molecular weight ε-poly-L-lysine obtained in Example 1 was used to evaluate the cytotoxicity to COS-1 (African green monkey kidney cell).

$5 \times 10^3$ cells/well of COS-1 (African green monkey kidney cell) was inoculated to a 96-well microplate and cultured in a DME medium (containing 10 w/v % fetal bovine serum) at 37° C. in 5 v/v % $CO_2$ overnight. Then, the medium was removed using an aspirator, and 40 μl/well of fresh medium having a concentration 1.25 times higher than the normal concentration was added. Each of the solution having various concentrations of the high molecular weight ε-poly-L-lysine (10 μl) were added thereto, followed by culturing at 37° C. for 3 hours. After completion of the culturing for 3 hours, the medium was removed using an aspirator, and 110 μl/well of a fresh medium was added, followed by preculturing at 37° C. in a 55 v/v % $CO_2$ incubator for 46 hours. The medium was exchanged, and 10 μl of WST assay (see the following document) solution (manufactured by Dojindo Laboratories, Cell-counting Kit-8) was added to each well, followed by culturing at 37° C. in a 5 v/v % $CO_2$ incubator for 2 hours to perform a color reaction. Then, absorbance at 450 nm (reference 650 nm) was measured using a plate reader (manufactured by ThermoLab Systems, MultiSkan Acent BIF) and cell viabilities were calculated.

Reference document: Ishiyama, M., Miyazono, Y., Sasamoto, K., Ohkura, Y., Ueno, K., Talanta, 44, 1299 (1997).

Figure 4:
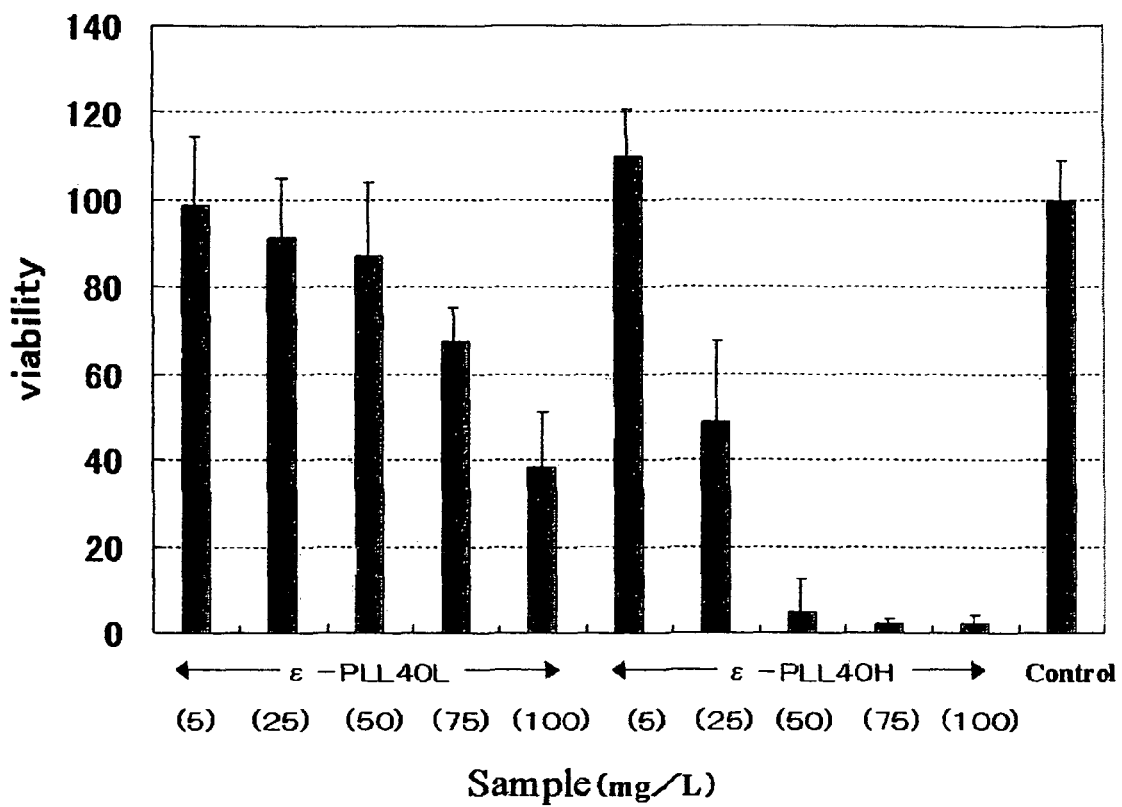
FIG. 4 shows the cell viabilities upon treatment with the high molecular weight ε-poly-L-lysine.

The results are shown in FIG. 4. In general, the cytotoxicity increases in proportion to a transfection activity. The results showed that the high molecular weight ε-poly-L-lysine had higher cytotoxicity than the non-high molecular weight ε-poly-L-lysine (ε-PLL). The cytotoxicity increases as the molecular weight increases, which is apparent for ε-PLL40H having a molecular weight of 50,000 or more. On the other hand, it should be noted that ε-PLL40L, which has a higher transfection activity than ε-PLL40H, has lower cytotoxicity than ε-PLL40H. The cytotoxicity of ε-PLL40L is rarely found under a normal transfection condition (10mg/l), and therefore, ε-PLL40L was confirmed to be highly safe.

Industrial Applicability

The high molecular weight ε-poly-L-lysine obtained by using the ε-poly-L-lysine represented by the Formula (I) strongly and electrostatically binds to a nucleic acid, resulting in formation of a complex. The nucleic acid complex has low cytotoxicity, can be prepared easily and inexpensively, and has a high transfection efficiency, and enables introduction of a nucleic acid into a cell or the like. Meanwhile, it can be utilized as a nonviral vector for a gene therapy using a plasmid DNA.

While the invention has been described in detail with reference to preferred embodiments thereof, it will be apparent to one skilled in the art that various changes can be made, and equivalents employed, without departing from the scope of the invention. Each of the aforementioned documents, including the foreign priority document, JP2005-129375, is incorporated by reference herein in its entirety.

The invention claimed is:

1. A nucleic acid complex, comprising a high molecular weight derivative of ε-poly-L-lysine and a plasmid DNA, wherein the high molecular weight derivative of ε-poly-L-lysine is obtained by dehydration-condensation of ε-poly-L-lysine subunits of Formula (I),

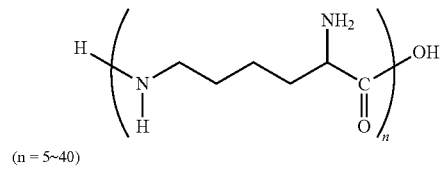

(n = 5~40)

and wherein the high molecular weight derivative of ε-poly-L-lysine has a molecular weight of 10,000 to 50,000 Da.

2. The nucleic acid complex according to claim 1, wherein the ε-poly-L-lysine subunits of Formula (I) are produced by microbial fermentation.

3. A method of introducing a nucleic acid into a cell, comprising administering the nucleic acid complex according to claim 1 to a cell.

* * * * *